(12) United States Patent
Yoshikawa et al.

(10) Patent No.: US 8,568,819 B2
(45) Date of Patent: *Oct. 29, 2013

(54) SOLID COMPOSITION CONTAINING LIPIDS FROM CRUSTACEANS

(75) Inventors: Kazuhiro Yoshikawa, Hachioji (JP); Akihiro Mikajiri, Hachioji (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/120,842

(22) PCT Filed: Sep. 24, 2009

(86) PCT No.: PCT/JP2009/066530
§ 371 (c)(1),
(2), (4) Date: Apr. 25, 2011

(87) PCT Pub. No.: WO2010/035750
PCT Pub. Date: Apr. 1, 2010

(65) Prior Publication Data
US 2011/0189760 A1     Aug. 4, 2011

(30) Foreign Application Priority Data
Sep. 26, 2008   (JP) ................ P2008-248986

(51) Int. Cl.
A23D 7/00      (2006.01)

(52) U.S. Cl.
USPC ........................................ 426/601

(58) Field of Classification Search
USPC ........................................ 426/601
See application file for complete search history.

(56) References Cited

U.S. PATENT DOCUMENTS

| | | | |
|---|---|---|---|
| 6,399,105 B1 * | 6/2002 | Collin | 424/550 |
| 6,800,299 B1 * | 10/2004 | Beaudoin et al. | 424/522 |
| 2003/0054084 A1 | 3/2003 | Hruschka et al. | |
| 2009/0061067 A1 | 3/2009 | Tilseth et al. | |
| 2010/0143571 A1 | 6/2010 | Breivik | |
| 2010/0226977 A1 | 9/2010 | Tilseth | |
| 2011/0189374 A1 | 8/2011 | Yoshikawa | |

FOREIGN PATENT DOCUMENTS

| | | |
|---|---|---|
| EP | 0 848 911 | 6/1998 |
| EP | 2 006 296 | 12/2008 |
| JP | 52-76455 | 6/1977 |
| JP | 52-114046 | 9/1977 |
| JP | 54-76858 | 6/1979 |
| JP | 2-215351 | 8/1990 |
| JP | 8-325192 | 12/1996 |
| JP | 10-179038 | 7/1998 |
| JP | 2909508 | 4/1999 |
| JP | 2003-003190 | 1/2003 |
| JP | 2004-026767 | 1/2004 |
| SU | 220741 | 10/1970 |
| WO | 00/23546 | 4/2000 |
| WO | 2007/080514 | 7/2007 |
| WO | WO 2007/080515 | * 7/2007 |
| WO | 2007/105734 | 9/2007 |
| WO | 2009/027692 | 3/2009 |

OTHER PUBLICATIONS

Sikorski E. et al. The Utilizationof Krill for Food. Food Process Engineering vol. 1 845-855, 1980.*
Edible oils and processing—"Saishin Shokuhin Kakou Koza—Shokuyo Yushi to Sono Kako" edited by Tetsujiro Ohara, published by Kenpakusha, 1981, pp. 49-74—machine translation.
Fish oil and sardine—"Gyoyu to Maiwasi" edited by Hichiro Matsushita, published by Koseisha Koseikaku, 1991, pp. 21-28—machine translation.
"Bailey's Industrial Oil and Fat Products" edited by Y. H. Hui, published by John Wiley & Sons, 1996, Fifth Edition, vol. 1, pp. 336-347.
Clarke, "The Biochemical Composition of Krill, *Euphausia superba* Dana, From South Georgia", J. exp. mar. Biol. Ecol., 1980, vol. 43, pp. 221-236.
Fedotova, et al., "Changes in the fatty acid composition of lipids in Okean krill paste during cooking", Vopr Pitan, No. 1, pp. 70-73, 1977, with English translation.
Sikorski, et al., "The Utilization of Krill for Food", Food Process Eng., vol. 1, 1980, pp. 845-855.
Osnes, et al., "Peptide Hydrolases of Antarctic Krill, *Euphausia superba*", Comp. Biochem. Physiol., vol. 82B, No. 4, pp. 599-606, 1985.

* cited by examiner

*Primary Examiner* — Ralph Gitomer
(74) *Attorney, Agent, or Firm* — Hamre, Schuman, Mueller & Larson, P.C.

(57) ABSTRACT

The present invention relates to a method for efficiently extracting and producing lipid components from crustaceans. A method for producing lipids, characterized by obtaining a squeezed liquid by squeezing a whole crustacean or a part thereof, heating the squeezed liquid to a temperature at which proteins contained in the squeezed liquid coagulate, carrying out solid-liquid separation so as to separate the heated squeezed liquid into a solid component that contains lipid components and an aqueous component that contains water-soluble components, washing the resulting solid containing lipids or a dried product thereof with water, dehydrating and/or drying, and then extracting lipids from the solid containing lipids or the dried product thereof.

4 Claims, 1 Drawing Sheet

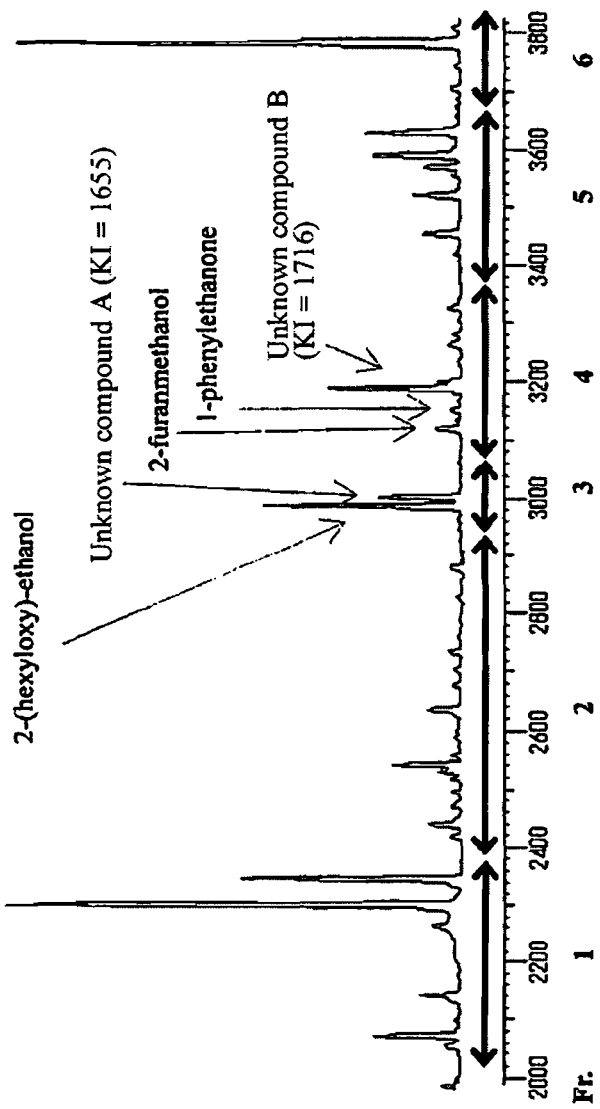

SOLID COMPOSITION CONTAINING LIPIDS FROM CRUSTACEANS

This application is a National Stage application filed under Rule 371 based upon PCT/JP2009/066530 filed Sep. 24, 2009.

TECHNICAL FIELD

The present invention relates to a method for efficiently producing lipids, and especially phospholipids, contained in crustaceans, and more specifically relates to a method for producing lipids without causing unpleasant odors.

BACKGROUND ART

Edible lipids have been manufactured industrially from old times. For example, in the case of soybean oil which is most abundantly manufactured at present, after washing soybean seeds, outer skins thereof are removed if necessary and then the soybean seeds are crushed/made flat by compression and extracted with an organic solvent using, in many cases, hexane of about 50 to 60° C. After that, the extract is filtered and the solvent is removed therefrom (by means of distillation in many cases) to give crude oil. The crude oil is further filtered or centrifuged to remove the insoluble fractions and water is added thereto to remove water-soluble substances (degumming) followed by carrying out the steps of deacidification, decolorization and deodorization to give a product. Usually, manufacture of lipids from a raw material containing high amount of lipids such as plant seeds is relatively easy (Non-Patent Document 1). On the other hand, in the case of animal raw materials, oil is usually separated out only by and heating of the raw material after washing. Therefore, the product is able to be more easily manufactured. In the case of fish for example, since a liquid part is spontaneously separated into an aqueous part and a crude oil when the raw material is boiled and squeezed, fish oil is able to be manufactured by purifying the oil (Non-Patent Document 2). However, the lipids prepared by the methods are mainly triglycerides.

It has been known that phospholipid, a class of the lipids, has health functions such as an improvement in fatty liver caused by choline deficiency, a reduction in LDL (bad cholesterol) in blood and an increase in HDL (good cholesterol) in blood. Additionally, improvement in neuropathy caused by hypertension and acetylcholine deficiency, promotion of absorption of oil-soluble vitamins, etc. is expected. Phospholipid has been mostly separated and purified from soybean seed or egg yolk. In the case from soybean seed, phospholipid is contained in a fraction which is removed as an insoluble matter during a degumming step in the manufacturing steps of soybean oil and it is decolorized and dried to obtain a phospholipid product called lecithin (Non-Patent Document 3). Soybean oil has a very big market and phospholipid as a by-product thereof is also produced in large quantities. In the case of egg yolk, since about one-third of its weight is lipids and about one-third of lipids are phospholipids, extraction and purification of phospholipid are relatively easy. However, in view of efficient extraction of phospholipid and maintenance of its stability, it is necessary that water is previously removed from the raw material egg yolk. Dried egg yolk is manufactured by inputting of heat cost and phospholipid is extracted therefrom.

With regard to other raw materials containing a relatively high amount of phospholipid, marine products such as marine fish egg and krill have been known. However, when those raw materials are compared with egg yolk, content of phospholipid in the raw material is low and other impurities such as organic acids are abundant. Therefore, purification is not easy. With regard to preparation of lipids from marine products, there have been various proposals up to now such as a method where the material is previously dried and then lipids are extracted therefrom, e.g., a raw material marine product is dried so as to make the water content 10% or less by weight and then lipids are extracted therefrom (Patent Document 1), a method where a raw material is dried by means of freeze-drying and then lipids are extracted therefrom (Patent Document 2), a method where an organic solvent is used, e.g., lipids are extracted from the raw material fish/shellfish with a mixed solution of acetone and water, (Patent Document 3) and a method where, in extraction of lipids from the starting krill, acetone is used as the first stage (Patent Document 4). However, any of those methods has problems such as difficulty in terms of cost, complicatedness in the steps and limitation in the use due to legal restrictions.

Highly unsaturated fatty acids have been known to have a preventing/improving activities for lifestyle-related diseases (such as arteriosclerosis, hyperlipemia and dementia) and an immunosuppressive activity (such as reduction in allergy and atopy). Furthermore, EPA is expected for its effect of prevention of circulatory diseases such as reduction in neutral fats and suppression of platelet aggregation while DHA is expected for its effect of growth and maintenance of function of nerve tissues and improvement in eyesight (Non-Patent Document 4). Lipids from marine products are promising not only as a supplying source for phospholipid but also as a supplying source for highly unsaturated fatty acids such as EPA and DHA. However, as mentioned above, marine products contain many impurities such as organic acids including amino acids and fatty acids. Therefore, extraction and purification of lipids therefrom have not been easy.

In the past, attempts have been made to extracts lipids containing highly unsaturated fatty acids from krill, a type of crustacean. Because krill contain large quantities of proteolytic enzymes, protein components in the krill rapidly decompose if attempts are made to concentrate lipids from krill in a state whereby heating is not carried out and proteins are not denatured (hereinafter called "unheated"), resulting in the formation of an emulsion with phospholipids, which are contained in large quantities in krill, which flow into the aqueous layer. As a result, it is difficult to recover lipids.

When concentrating lipids from krill in the past, ground krill was dried in order to obtain a krill meal, from which lipids were concentrated, but when this method was used, unpleasant odors were generated during the drying process, meaning that it was difficult to obtain edible lipids. In addition, because large quantities of ash were generated during refining, depending on the method used, ash often adhered to the apparatus, thereby causing corrosion and preventing the apparatus from operating continuously.

On the other hand, a method in which proteins are obtained by coagulating protein components in krill, which is a type of crustacean, by heating has been known in the past as a method for extracting proteins from krill (patent document 5). However, a coagulated product known as "Okean" obtained by this method was used in order to obtain proteins, and it was not used to obtain lipids (non-patent document 5).

In addition, after the present application was filed, a method for obtaining a coagulated product by heating krill to 60 to 70° C. by means of hot water and then reheating the thus obtained aqueous solution of the supernatant liquid to 90° C. or higher was disclosed within the priority claim period (patent document 6).

Patent Document 1: JP08-325,192 A
Patent Document 2: JP2,909,508 B
Patent Document 3: JP2004-26767 A
Patent Document 4: WO 00/23546
Patent Document 5: SU227041
Patent Document 6: WO 09/027692
Non-Patent Document 1: "Saishin Shokuhin Kakou Koza—Shokuyo Yushi to Sono Kako" edited by Tetsujiro Ohara, published by Kenpakusha, 1981, pages 49 to 74
Non-Patent Document 2: "Gyoyu to Maiwasi" edited by Hichiro Matsushita, published by Koseisha Koseikaku, 1991, pages 21 to 28
Non-Patent Document 3: "Bailey's Industrial Oil and Fat Products" edited by Y. H. Hui, published by John Wiley & Sons, 1996, Fifth Edition, Volume 1, page 336
Non-Patent Document 4: A. Clarke, *Journal of Experimental Marine Biology and Ecology*, 1980, Volume 43, No. 3, pages 221 to 236
Non-Patent Document 5: Vopr Pitan, No. 1, page 70 to 73, 1977

DISCLOSURE OF THE INVENTION

Problems to be Solved by the Invention

The present invention is made to solve the previous problems of efficiently producing lipids, and especially phospholipids, from crustaceans. In particular, the present invention is made to solve the previous problems of producing lipids of a quality that is preferred for use in foods such as odorless supplements.

Means for Solving the Problems

Under such a current status as described above, the inventors of the present invention have carried out intensive investigations repeatedly for a method of easy separation and concentration of lipids derived from crustaceans. As a result, they have found that lipids are localized in a solid part when a liquid part of crustaceans such as internal organs other than shells and muscles and internal tissues of the cephalothorax is previously separated and recovered by squeezing and the liquid part containing water-soluble impurities is heated to thermally coagulate proteins therein. Furthermore, they found that the impurities such as water-soluble organic acids, amino acids and peptides are able to be removed from the solid part by a simple means such as filtration and centrifugal separation. As a result, the present invention has been achieved.

Features of the present invention are as follows:

[1] A method for producing lipids, characterized by obtaining a squeezed liquid by squeezing a whole crustacean or a part thereof, heating the squeezed liquid to a temperature at which proteins contained in the squeezed liquid coagulate, carrying out solid-liquid separation so as to separate the heated squeezed liquid into a solid component that contains lipid components and an aqueous component that contains water-soluble components, washing the resulting solid containing lipids or a dried product thereof with water, dehydrating and/or drying, and then extracting lipids from the solid containing lipids or dried product thereof.

[2] The method described in [1], wherein the washing with water is carried out using a quantity of water equivalent to at least four times the weight of the solid containing lipids or dried product thereof.

[3] The method described in [1] or [2], wherein the washing with water is carried out at least twice.

[4] The method described in any one of [1] to [3], wherein the solid containing lipids or dried product thereof is cut to a diameter of not less than 1 cm and not more than 10 cm and then washed with water.

[5] The method described in any one of [1] to [4], wherein the washing with water and/or dehydration is carried out after placing the solid containing lipids or dried product thereof in a mesh bag.

[6] The method described in any one of [1] to [5], wherein the washing with water is carried out to an extent whereby odors from components adsorbed on an adsorbent that adsorbs volatile components having molecular weights of 100 to 200 cannot be sensed.

[7] The method described in any one of [1] to [5], wherein the washing with water is carried out to an extent whereby an ash content is 5% or less of a dry weight of the lipid-containing dried product.

[8] The method described in any one of [1] to [7], wherein the method for extracting lipids is any one of organic solvent extraction, enzyme treatment followed by organic solvent extraction, or supercritical fluid extraction.

[9] The method described in any one of [1] to [8], wherein the crustacean used is one belonging to the order Euphausiacea.

[10] A composition containing lipids obtained using a method described in any one of [1] to [9].

[11] The composition containing lipids described in [10], from which components adsorbed using a column that adsorbs volatile components having molecular weights of 100 to 200 are removed to an extent whereby odors from these components cannot be sensed in a sensory test.

Effect of the Invention

According to the present invention, it is possible to simply and inexpensively produce lipids that contain large quantities of phospholipids from crustaceans. In particular, it is possible to produce lipids that do not cause unpleasant odors, have a low ash content and do not cause corrosion.

BRIEF DESCRIPTION OF THE DRAWINGS

FIG. 1 is a chromatogram obtained in working example 18.

BEST MODE FOR CARRYING OUT THE INVENTION

The present invention relates to a method for concentrating lipids contained in crustaceans, which comprises heating a squeezed liquid prepared by squeezing the whole crustacean or a part thereof is heated and carrying out a solid-liquid separation into a solid which comprises lipid components and liquid which comprises water-soluble components. Although there is no particular limitation for the crustaceans which are a raw material of the present invention as long as it belongs to the class Malacostraca (a class to which shrimp, etc. belong), that which belongs to the order of Euphausiaceae or Decapodoceae is particularly used. Specifically, krill, shrimp, crab, etc. can be used and a part thereof such as cephalothorax of shrimps, shrimp shell meal and krill meal may be used as well. In that case, although there is no particular limitation for the type of the krill, *Euphausia pacifica* is particularly favorably used. Although the raw material may be heated and unheated as long as it is in a state which contains the lipids, it is preferable to use an unheated raw material such as fresh fish (raw one), frozen one or a raw material where the frozen one is thawed.

With regard to a method for squeezing, there is no particular limitation as long as it is a commonly used one. For example, an oil hydraulic squeezing machine, a screw press, a meat separator, a press dehydrating machine, a centrifugal separator or a combination thereof can be used. When collection of the lipids is an object, it is preferable that the whole crustacean or a part thereof is squeezed to obtain a squeezed liquid corresponding to an amount of 5 to 50% of the wet weight. When the squeezing is 5% or less, the lipids are not sufficiently compressed and extracted. When it is 50% or more, although the lipids are sufficiently squeezed, other impurities such as water-soluble organic acids, amino acids, peptides and proteins are contaminated and the steps for separation and extraction of the lipids thereafter become troublesome. However, when preparation of a solid containing the lipid component is an object, there is no problem even when the squeezing is conducted to an extent of 50% or more. Additionally, the shells after the squeezing produced in the preparation of squeezed liquid may be utilized as an ingredient of a feed, etc. according to a common utilizing method for krill.

After that, the resulting squeezed liquid is heated. There is no particular limitation for the heating method and any of commonly used methods can be used. Temperature for the heating may be temperature at which proteins are coagulated. For example, it is 50° C. or more and, it is preferably from 70 to 150° C. and particularly preferably from 85 to 110° C. Heating may be carried out under pressure or in vacuo. As a result, separation into a solid which comprises the lipid components and liquid which comprises water-soluble components is carried out. When a solid-liquid separation is carried out by means of, for example, filtration or centrifugal separation, solids containing the lipids (hereinafter, it may be referred to as the thermally coagulated product) can be obtained.

Lipids are extracted from this solid containing lipids or a dried product thereof. The method for extracting the lipids is not particularly limited as long as a commonly used method is used, but it is possible to use solvent extraction, separation and removal of protein components by means of a pH adjusting agent or an enzyme such as a protease or lipase, supercritical fluid extraction and the like, or a combination thereof, with extraction using an organic solvent, enzyme treatment followed by extraction using an organic solvent or extraction using supercritical carbon dioxide being preferred. Extraction with organic solvent, extracting with organic solvent after enzymatic treatment or supercritical extraction with carbon dioxide is preferably used. With regard to solvent used for the extraction with solvent, an appropriate organic solvent such as alcohol (e.g., methanol, ethanol, propanol, isopropanol, butanol, propylene glycol and butylene glycol), methyl acetate, ethyl acetate, acetone, chloroform, toluene, pentane, hexane, cyclohexane, etc. may be used solely or jointly by combining two or more thereof. Mixed liquid of ethanol or hexane with ethanol is preferably used to extract the lipids. At that time, a mixing ratio of the solvents or a ratio of the material to the solvent may be freely set. With regard to the enzyme used for the enzymatic treatment, although there is no particular limitation as long as it is able to be used for foods, protease such as Alkalase (registered trade mark) (manufactured by Novozymes), protease A, M or P, pancreatin F (manufactured by Amano Enzyme), etc are used. The pH, the temperature condition, etc. for the enzymatic treatment can be set depending on the enzyme used and, for example, the method which is described in "Atarashii Shokuhin Kako Gijutsu I" edited by Takashi Yamashita (Kogyo Gijutsukai, 1986, pages 204 to 284) may be referred to. With regard to the supercritical extraction method using carbon dioxide, it may be carried out according to a common method and, for example, the method mentioned in "Atarashii Shokuhin Kako Gijutsu I" edited by Takashi Yamashita (Kogyo Gijutsukai, 1986, pages 79 to 102) may be referred to. In accordance with the above-mentioned methods, the lipids containing a lot of phospholipid are able to be manufactured from crustaceans easily and at a low cost.

In the solids containing lipids prepared by the above-mentioned method, the lipids are concentrated in an efficient manner. The solids containing lipids contains 35% by weight or more, preferably contains 40% by weight or more of lipids in the total solid. The feature of the solid is that 40% or more by weight of the lipids as are phospholipids. The solids containing lipids or a dried product thereof or the lipids which are extracted therefrom by the above-mentioned method contain(s) the phospholipid abundantly. The lipids which further contain highly unsaturated fatty acids such as EPA and DHA is prepared which is able to be used as a material for pharmaceuticals, an ingredient for food or feed.

A method for drying the solid may be in accordance with the common method. For example, it is possible to carry out hot air drying or drying by means of steam. In addition, drying may be carried out by heating with high frequency waves or microwaves, vacuum/reduced pressure drying, freezing and thawing, or by means of a desiccant, and these methods may be used in combination. Because oxidized lipids cause unpleasant odors if the temperature is too high during the drying process, the drying should be carried out at 90° C. or lower, preferably 75° C. or lower, and more preferably 55° C. or lower. The drying may be carried out after preparing the solid containing lipids or after the under-mentioned washing with water (hereinafter, a product obtained by washing with water and then drying is called a washed and dried product). In cases where caught krill are used to prepare solids containing lipids at sea, the drying should be carried out prior to transport for reasons of transport costs. In view of the performance of the equipment and so on, if the drying is being carried out at sea, it is possible to stop part way through the drying process, land, and then restart the drying process on land. The reason for this is that as long as no unpleasant odors are generated due to the lipid-containing solids being exposed to high temperatures between the drying process carried out at sea and the drying process carried out on land, it is possible to eliminate krill odor and the source of the unpleasant odors by subsequent washing with water. In addition, because there are concerns regarding the krill putrefying in the case of long transport periods, it is preferable to refrigerate or freeze the krill before transportation.

By subjecting solids containing lipids obtained using the above-mentioned method to further washing with water, it is possible to eliminate the sources of krill odors and unpleasant odors. Krill odors and unpleasant odors are a particular problem when using concentrated lipids in foods. It is difficult to eliminate these odors from lipids after extraction has been carried out. In addition, phospholipids are naturally water-soluble and lipid-soluble, and cannot be washed with water without being subjected to some form of fixation. Therefore, in order to eliminate odorous components by washing with water, it is necessary to use a water-insoluble support to which odorous component are not adsorbed but to which phospholipids are adsorbed. In the present invention, it was found that thermally coagulated products of proteins contained in the squeezed krill liquid were suitable for use as this type of support, and non-odorous lipids are concentrated from krill by making use of this property.

In the present invention, volatile components adsorbed in a column are specified as being the source of krill odors and unpleasant odors. Specifically, the source of krill odors and unpleasant odors in the present invention can be adsorbed in a column that adsorbs volatile components having molecular weights of 100 to 200, preferably a column that adsorbs volatile components having molecular weights of 100 to 150, and more preferably adsorption can be by Porapak Q, and no odors will remain in the lipids following adsorption. When carrying out the adsorption, lipids that have been subjected to distillation at less than or equal to 60° C. for 30 minutes or longer should be passed through the column, and in order to prevent bumping, it is preferable to increase the temperature gradually from 25° C. However, eliminating components that are sources of krill odors and unpleasant odors from lipids by a column adsorption method involves a great deal of effort and cost, and is therefore not practical. Therefore, eliminating these odor sources by the simple process of washing with water, as in the present invention, is very practical.

By subjecting solids containing lipids obtained using the above-mentioned method to washing with water, it is possible to further remove some of the ash and water-soluble proteins. Ash mainly comprises sodium chloride, potassium, and calcium chloride that are contained in bodily fluids and sea water that adheres to body surfaces. In the lipid concentration process, chlorine salts can precipitate as chlorine salts during drying or distillation. Like phospholipids, most of the ash is soluble in water. Therefore, it is possible to remove most of the ash by washing with water under conditions by which phospholipids are not dissolved.

In particular, if sodium chloride is precipitated, metal equipment such as the concentrating apparatus is easily corroded. Therefore, the content of sodium chloride in the precipitated ash should be as low as possible. As a method for reducing the relative quantity of sodium chloride, it is possible to squeeze all or a part of the crustaceans and dissolve calcium contained in the shells. With regard to a method for squeezing, there is no particular limitation as long as it is a commonly used one. For example, an oil hydraulic squeezing machine, a screw press, a meat separator, a press dehydrating machine, a centrifugal separator or a combination thereof can be used. As the degree of squeezing increases, the relative quantity of calcium chloride increases and the relative quantity of sodium chloride decreases, but if the degree of squeezing is excessive, problems relating to lipid concentration occur, as mentioned above. Therefore, in order to reduce the relative quantity of sodium chloride in the ash contained in the lipids, all or a part of the crustaceans should be squeezed in such a way that a quantity of squeezed liquid equivalent to 5 to 50% of the wet weight is obtained. With methods in which all or a part of the crustaceans is not squeezed, most of the content of the ash is sodium chloride, and such methods are therefore not suitable for achieving the objective in question.

In order to remove ash from components obtained by thermally coagulating a squeezed liquid obtained in this way, washing with water is effective. Chlorine salts in the ash are soluble in water, but are hardly eluted when held within solids containing lipids. As a result, it is preferable to finely grind the solids containing lipids. By washing solids containing lipids with water in this way, it is possible to reduce the ash content to 10% or lower, and preferably 5% or lower. In addition, it is possible to reduce the sodium chloride content in the ash to 40% or lower, preferably 30% or lower, more preferably 20% or lower, and further preferably 10% or lower.

In addition, water-soluble proteins include both proteins that are naturally water-soluble and a variety of proteins that are modified by being heated, but examples thereof include actin, myosin, troponin, tropomyosin, ATPase, and calmodulin. By washing with water, 5% or more, preferably 10% or more, and more preferably 20% or more, of the proteins are washed out relative to the solids containing lipids prior to the washing with water. As a result of removing some of the ash and proteins, it is possible to increase the lipid content in terms of dry weight in the solids containing lipids by 5% or more, preferably 10% or more, and more preferably 15% or more, and further preferably 20% or more, relative to the lipid content in the solids containing lipids prior to washing with water. In addition, it is possible to make the proportion of lipids in the solids containing lipids 45% or higher, and preferably 50% or higher.

The amount of washing with water should be such that no odors can be sensed in a sensory test. The washing with water in order to eliminate krill odor components, ash, and water-soluble proteins is carried out with a quantity of fresh water or sea water equivalent to at least 4 times, and preferably at least 10 times, the dry weight of the solids containing lipids. The washing with water is preferably carried out at least twice, and more preferably at least three times. The washing with water can be carried out by injecting water into a container that contains the solids containing lipids, leaving for at least 5 minutes, and then separating off the aqueous fraction. Depending on the form of the solids containing lipids, a sufficient degree of agitation can also be effective. In addition, the washing with water can be carried out by allowing water to pass through a container that contains the solids containing lipids. Because solids containing lipids obtained using the method mentioned above are insoluble in water, it is possible to eliminate sources of krill odors and unpleasant odors, ash, and water-soluble proteins to a greater extent by increasing the amount of washing with water, but it is preferable to restrain the solids containing lipids with a fine mesh in order to prevent pieces of the solid containing lipids from being washed away during the washing. The fineness of the mesh should be such that clogging does not occur, and is preferably 1 mm or lower, and more preferably 250 μm or lower. In addition, because it is difficult to eliminate sources of odors if the pieces of the solids containing lipids are too large, the solids containing lipids should be finely ground. The solids containing lipids should preferably be crushed to a diameter of 10 cm, and more preferably 5 cm. However, the diameter should not be 1 cm or less in order to prevent pieces from being washed away.

The solids containing lipids can have a variety of specific gravities depending on the relative proportions of proteins, which have higher specific gravities than water, and lipids, which have lower specific gravities than water. Therefore, even if centrifugal separation is carried out following the washing with water, it is not possible to effectively remove the aqueous fraction. Separation of the aqueous fraction is preferably carried out by squeezing the solids containing lipids by means of a squeezing apparatus such as a screw press, by a free fall method in which the solids containing lipids are restrained by a suitably fine mesh, or by means of centrifugal separation that uses a centrifuge tube segmented by a mesh or a centrifuge tube in which the solids containing lipids are held in a mesh bag. In this way, it is possible to eliminate odorous components, ash, and/or water-soluble proteins from the solids containing lipids.

In addition, solids containing lipids obtained using the method mentioned above contain large quantities of astaxanthin. In crustaceans, astaxanthin is largely contained in tissue within crustaceans, and because breakdown of tissue within crustaceans is insufficient if only heat treatment is carried out, it is possible to concentrate lipids that contain large quantities of astaxanthin by squeezing krill. With regard to a method for squeezing, there is no particular limitation as long as it is a commonly used one. For example, an oil hydraulic squeezing machine, a screw press, a meat separator, a press dehydrating machine, a centrifugal separator or a combination thereof can be used. Increasing the degree of squeezing increases the degree of breakdown of the tissue within the crustaceans and increases the astaxanthin concentration in the lipids, but if the degree of squeezing is excessive, problems relating to lipid concentration occur, as mentioned above. Therefore, in order to increase the quantity of astaxanthin contained in the lipids and therefore facilitate concentration of the lipids, it is preferable that the whole crustacean or a part thereof is squeezed to obtain a squeezed liquid corresponding to an amount of 5 to 50% of the wet weight. With methods in which the whole crustacean or a part thereof is not squeezed, it is not possible to obtain the astaxanthin contained in the tissue within the crustaceans, and such methods are therefore not suitable for achieving this type of objective. Of the lipids contained in solids containing lipids obtained in this way, it is possible for the astaxanthin content to be 100 ppm, and preferably 150 ppm.

The lipid-containing solids of the present invention are a composition that contains lipids and proteins derived from a squeezed liquid of crustaceans, which can contains 30 wt. % or higher, and preferably 40 wt. % or higher, of lipids. Furthermore, by washing with water, it is possible to reduce the sodium chloride content in the ash to 40% or lower. Furthermore, the content of astaxanthin is 100 ppm or higher. The lipids in the lipid-containing solids of the present invention contain 50 wt. % or more of phospholipids and 15 wt. % or more of EPA and/or DHA. This composition contains the lipids which abundantly contain phospholipid and highly unsaturated fatty acids such as EPA and DHA. The lipids may be used as a material for pharmaceuticals, an ingredient for food or feed, etc.

Although Examples of the present invention will be described as follows, the present invention is not limited thereto.

EXAMPLE 1

Preparation of Squeezed Liquid of Krill (by a Batch Method) and a Heating Treatment Antarctic krill of at least 45 mm length (400 kg) collected in the Antarctic Ocean in late July of 2005 followed by an immediate freezing at −30° C. was thawed by airing at room temperature (15° C.). The thawed krill was squeezed using an oil hydraulic squeezing machine (manufactured by Tokyo Techno; material cell=about 2 cm' about 68 cm' about 40 cm height) with a squeezing rate (yield of the squeezed liquid to the supplied amount of the thawed krill) of 13% by weight (lot 1) or 26% by weight (lot 2). The squeezed liquid was combined with the previously prepared thawed drips and heated in a steaming type heating kettle (kneader) having a capacity of 1 ton. The heating was stopped when the temperature reached to 95° C. and the resulting thermally coagulated product (a solid containing lipids) was classified using a commercially available sieve basket made of stainless steel by means of a natural dropping. The thermally coagulated product was dried using a vacuum drier of a steam heating type (Ribocone manufactured by Okawara Mfg.; type RM 200 VD) to give 9.0 kg (lot 1) or 15.9 kg (lot 2) of a dried product. Components in the raw material krill and in the resulting dried thermally coagulated products are shown in Table 1.

TABLE 1

|  |  | Raw material | Dried Thermally Coagulated Product | |
|---|---|---|---|---|
|  |  |  | Lot 1 | Lot 2 |
| Squeezing Recovery | (wt %) | — | 13 | 26 |
| Water | (wt %) | 80.9 | 1.8 | 2.0 |
| Total Lipids | (dry wt %) | 17.4 | 51.2 | 51.8 |
| Crude Proteins | (dry wt %) | 67.7 | 40.1 | 40.1 |
| Ash | (dry wt %) | 15.6 | 8.7 | 8.1 |

As a result, it was confirmed that the lipids were efficiently concentrated from crustaceans by the method of the present invention. Then the lipids in the resulting thermally coagulated product (solids containing lipids) were analyzed. The resulting lipid composition and the representative fatty acid composition are shown in Table 2. With regard to the lipid composition, each lipid component separated by a developing solvent of benzene:chloroform:acetic acid (150:60:1.5) was quantified using a thin-layer automatic detecting device (manufactured by Mitsubishi Kagaku Iatron; type Iatroscan (registered trade mark) MK-6). With regard to the fatty acid composition, the constituting fatty acids were made into methyl esters in boron trifluoride and analyzed by a gas chromatography (Agilent Technologies; type 6890 N). The column for the gas chromatography used therefor was DB-WAX (Catalog No. 122-7032) of J & W Scientific. With regard to a carrier gas, helium was used and hydrogen flame ionization detector was used as a detector.

The dried product of the present thermally coagulated product did not show denaturation based on judgment by way of smell, color, etc. even when it is stored at room temperature for one year and the lipid component thereof was not oxidized but was retained stably. Further, as shown in Tables 1 and 2, the components of the thermally coagulated product of the present invention are useful as ingredients for livestock and marine feeds.

TABLE 2

|  |  | Lot 1 | Lot 2 |
|---|---|---|---|
| Lipid Composition | Triglycerides | 33 | 40 |
|  | Free Fatty Acids | trace | trace |
|  | Phospholipid | 67 | 59 |
| Fatty Acid Composition | C14:0 | 12.1 | 12.0 |
|  | C16:0 | 20.1 | 20.0 |
|  | C18:1 | 17.5 | 17.7 |
|  | C18:2 | 2.0 | 1.9 |
|  | C18:3 | 1.3 | 1.2 |
|  | C18:4 | 3.3 | 3.2 |
|  | EPA | 11.7 | 11.8 |
|  | DHA | 5.5 | 5.6 |

EXAMPLE 2

Preparation of Squeezed Liquid of Krill (by a Screw Press) and Heating Treatment The same krill as in Example 1 was thawed by airing at room temperature (8° C.) and the thawed drips were removed therefrom. The resulting thawed hill was placed in a screw press dehydrating machine (manufactured by Fukoku Kogyo; type SHZ-200' 1.5 ML) and treated with squeezing liquid rates (yields of the squeezed liquid to the supplied amount of the thawed krill) of 17 to 36% by weight to prepare squeezed liquids (lots 3 to 6). About 5 kg of each of the squeezed liquids was heated in a 50 L a steaming type heating kettle (rice boiler), heating was stopped when the temperature was confirmed to reach 95° C. The resulting thermally coagulated product (solids containing lipids) was classified using a commercially available sieve basket made of stainless steel by means of a natural dropping. Yield and components in the resulting thermally coagulated product of each lot are shown in Table 3. The yield is given in terms of the ratio by weight to the thawed raw material used. Moreover, dry weight (%) means the weight percentage of each component relative to the weight obtained by subtracting the weight of water from the overall weight (unless indicated otherwise, this is also the case in the following examples).

TABLE 3

|  |  | Thermally Coagulated Product | | | |
| --- | --- | --- | --- | --- | --- |
|  |  | Lot 3 | Lot 4 | Lot 5 | Lot 6 |
| Squeezing Recovery | (wt %) | 36 | 32 | 20 | 17 |
| Yield | (wt %) | 10.7 | 10.2 | 6.3 | 6.3 |
| Water | (wt %) | 65.5 | 69.1 | 65.7 | 66.1 |
| Total Lipids | (dry wt %) | 49.9 | 46.8 | 50.7 | 51.0 |
| Crude Proteins | (dry wt %) | 42.3 | 45.1 | 41.4 | 41.1 |
| Ash | (dry wt %) | 7.8 | 8.1 | 7.9 | 7.9 |

As a result, it was confirmed that the lipids were efficiently concentrated from crustaceans by the method of the present invention. Furthermore, the lipids in the resulting thermally coagulated product (solids containing lipids) were analyzed in the same manner as in Example 1. The results are shown in Table 4 and Table 5, respectively.

TABLE 4

|  |  | Lot 4 | Lot 5 |
| --- | --- | --- | --- |
| Lipid Composition | Triglycerides | 31 | 34 |
|  | Free Fatty Acids | 8 | 8 |
|  | Phospholipid | 59 | 57 |

TABLE 5

|  |  | Lot 3 | Lot 6 |
| --- | --- | --- | --- |
| Fatty Acid Composition | C14:0 | 11.4 | 11.5 |
|  | C16:0 | 20.1 | 20.0 |
|  | C18:1 | 17.7 | 17.8 |
|  | C18:2 | 1.9 | 1.8 |
|  | C18:3 | 1.2 | 1.2 |
|  | C18:4 | 2.9 | 2.9 |
|  | EPA | 13.1 | 13.2 |
|  | DHA | 6.8 | 6.7 |

EXAMPLE 3

Preparation of Squeezed Liquid from Krill (by a Meat Separator) and Heating Treatment 10 tons of Antarctic krill of at least a 45 mm length collected in the Antarctic Ocean in mid-July of 2006 was squeezed using a meat separator (manufactured by Baader; type: BAADER 605) immediately after fishing to give 3 tons of squeezed liquid. It was immediately frozen. The frozen squeezed liquid was heated in a steaming type heating kettle and the heating was stopped when temperature reached 95° C. The whole heating product was placed into a centrifugal dehydrating machine (manufactured by Taieiseisakusho; type DT-1) using a filter cloth of 200 meshes and an extract (filtrate) was separated to give a thermally coagulated product (solids containing lipids). Components in the raw material and in the thermally coagulated product are shown in Table 6.

TABLE 6

|  |  | Raw material | Thermally Coagulated Product |
| --- | --- | --- | --- |
| Water | (wt %) | 81.6 | 60.4 |
| Total Lipids | (dry wt %) | 31.7 | 46.7 |
| Crude Proteins | (dry wt %) | 56.0 | 47.0 |
| Ash | (dry wt %) | 12.3 | 6.3 |

As a result, it was confirmed that the lipids were efficiently concentrated from crustaceans by the method of the present invention. Furthermore, the lipids in the resulting thermally coagulated product (solids containing lipids) were analyzed in the same manner as in Example 1. The result is shown in Table 7.

TABLE 7

|  |  | Raw material | Thermally Coagulated Product |
| --- | --- | --- | --- |
| Lipid Composition | Triglycerides | 30 | 31 |
|  | Free Fatty Acids | 2 | trace |
|  | Phospholipid | 66 | 65 |
| Fatty Acid Composition | C14:0 | 11.8 | 12.0 |
|  | C16:0 | 22.4 | 22.8 |
|  | C18:1 | 19.8 | 20.0 |
|  | C18:2 | 1.7 | 1.6 |
|  | C18:3 | 1.0 | 1.0 |
|  | C18:4 | 1.7 | 1.7 |
|  | EPA | 13.6 | 13.1 |
|  | DHA | 6.6 | 6.0 |

EXAMPLE 4

Extraction of Lipids from a Thermally Coagulated Heated Squeezed Liquid Using Chloroform Dried product (10 g) of the thermally coagulated product (solids containing lipids) prepared in Example 3 was homogenized in 100 mL of chloroform to give an extract oil 3.71 g. The extract oil was adsorbed with a column of silica gel (manufactured by Asahi Glass; Microsphere Gel; catalog number MS Gel Sil; 300 g) and then neutral lipids, etc. were washed with chloroform. After that, moving bed was changed to be methanol to recover 0.228 g of phospholipid. Analytical value of the lipids in 10 g of the dried thermally coagulated product was 4.72 g. The resulting phospholipid was tested with an Introscan analyser (the developing solvent comprises chloroform, methanol and water in 65:25:4). The phospholipid was found to be composed of 96% by weight of phosphatidylcholine and 4% by weight of phosphatidyl ethanolamine. Fatty acid composition of the phospholipid prepared in the Example was also analyzed by the same way as in Example 1. The result is shown in Table 8.

TABLE 8

| Fatty Acids | Total Lipids (Extract Oil) | Phospholipid |
|---|---|---|
| C14:0 | 12.0 | 2.3 |
| C16:0 | 22.8 | 26.1 |
| C18:1 | 20.0 | 10.4 |
| C18:2 | 1.6 | 2.1 |
| C18:3 | 1.0 | 1.4 |
| C18:4 | 1.7 | 1.6 |
| EPA | 13.1 | 29.7 |
| DHA | 6.1 | 12.1 |

As a result, it was confirmed that, when only phospholipid was taken out from the extract oil, purity of highly unsaturated fatty acids such as EPA and DHA became high.

EXAMPLE 5

Extraction of Lipids from Coagulated Product of Heated Squeezed Liquid Using Hexane-Ethanol Lipids were extracted from 2.00 g of a dried product (analytical value of total lipid content was 0.94 g) of the thermally coagulated product (the solids containing lipids) prepared in Example 3 with 50 mL of a hexane-ethanol mixture (the solids containing lipids:solvent=1:25). The lipids were used for an extraction where the mixing ratio of the two kinds of solvents was varied from 100:0 to 0:100 to compare the extracting efficiency. Yield of the extract oil and purity of the phospholipid used in a lipid analysis by an Iatroscan analyzer are shown in Table 9.

TABLE 9

| | | | | | | | | |
|---|---|---|---|---|---|---|---|---|
| Hexane | (vol %) | 100 | 80 | 60 | 50 | 40 | 20 | 0 |
| Ethanol | (vol %) | 0 | 20 | 40 | 50 | 60 | 80 | 100 |
| Extract Oil | (g) | 0.79 | 0.89 | 0.97 | 0.97 | 0.94 | — | — |
| Extraction Yield | (wt %) | 84 | 94 | 103 | 103 | 100 | — | — |
| Purity | (%) | 55 | 65 | 66 | 65 | 64 | 67 | 65 |

As a result, when a mixing ratio of hexane was 20% or less in the test, water remained in the removal of the solvent from the extract oil by a vacuum concentration whereby an emulsion was formed and, therefore, no yield was determined. However, when the mixing ratio of hexane was from 40 to 80%, the lipids were able to be recovered in a yield of 90% or higher. On the other hand, it was confirmed that purity of the phospholipid in the extract oil was almost constant in any mixing ratio of the solvents other than the case where 100% of hexane was used.

EXAMPLE 6

Investigation of Solvent Amount in Extraction with Solvent

Dried product of the thermally coagulated product (the solids containing lipids) prepared from the squeezed liquid of krill in Example 3 was used and the same procedure as in Example 6 was carried out using a solvent comprising hexane and ethanol in a mixing ratio of 60:40 to obtain extracted oil. However, ratio of the material, solid containing lipids, to the solvent was varied from 1:5 to 1:20. The analytical result for the extracted oil is shown in Table 10.

TABLE 10

| Ratio of Material:Solvent | 1:5 | 1:10 | 1:20 |
|---|---|---|---|
| Extraction Yield (wt %) | 75 | 86 | 94 |
| Purity of phospholipid (%) | 61 | 59 | 63 |

As a result, it was confirmed that purity of the phospholipid in the extract oil was almost constant even when the ratio of the solvents was varied.

EXAMPLE 7

Separation of Extracted Oil in the Thermally Coagulated Product by a Treatment with Protease Distilled water (30 g) was added to 3 g of the thermally coagulated product (the solids containing lipids) prepared in Example 3 and a homogenizing treatment was carried out. The thermally coagulated product was uniformly dispersed. To the liquid (pH 7.5), 1 mL of a commercially available liquid enzyme (Alkalase 2.4 L; manufactured by Novozymes) or 1 mg of a commercially available powdery enzyme (Protease A, Protease M, Protease P or Pancreatin F manufactured by Amano Enzyme) and an enzymatic reaction was carried out at 50° C. for 2 hours. After that, pH of the reaction solution was adjusted to 1.4 using 2N hydrochloric acid and the solution was separated by centrifugation (2230 g for 10 minutes) at 50° C. The whole liquid layer containing the oil separated out in the surface layer was recovered. Each of the lipids contained in the whole liquid layer and in the precipitate was quantified by a mixed solvent comprising chloroform and methanol (2:1) and the recovering rate was determined. The result is shown in Table 11.

TABLE 11

| (wt %) | Liquid Layer | Precipitate | Total |
|---|---|---|---|
| No Enzyme | 24 | 82 | 106 |
| Alkalase | 40 | 67 | 107 |
| Protease A | 31 | 72 | 103 |
| Protease M | 27 | 72 | 99 |
| Protease P | 34 | 71 | 105 |
| Pancreatin F | 28 | 71 | 99 |

As a result, it was confirmed that liberation of the lipids from the thermally coagulated product (the solids containing lipids) to a liquid layer proceeded when an enzymatic treatment was carried out.

EXAMPLE 8

Extraction of Lipids from the Thermally Coagulated Product by Supercritical Carbon Dioxide The thermally coagulated product (the solids containing lipids where the water content was 61.2% by weight) prepared in Example 3 or a dried product thereof (water content was 2.0% by weight) was used and an extraction of the lipid component using supercritical carbon dioxide was carried out under the condition of 34.3 MPa and 40° C. to give an extract and a residue after the extraction. The result is shown in Table 12.

TABLE 12

|  | Materials for Extraction | |
|---|---|---|
|  | Thermally Coagulated Product | Dried Thermally Coagulated Product |
| Amount of the Materials Used (g) | 103.7 | 101.9 |
| Extracted Amount (g) | 40.3 | 24.5 |
| Recovered Amount of Residue (g) | 79.2 | 77.4 |

Lipid composition was analyzed by the same manner as in Example 1 for the lipids in the resulting extract and in the residue after extraction. The result is shown in Table 13. In the table, TG, FFA and PL mean triglycerides, free fatty acids and phospholipid, respectively.

TABLE 13

|  |  | Materials for Extraction | |
|---|---|---|---|
|  |  | Thermally Coagulated Product | Dried Thermally Coagulated Product |
| Extract | Triglycerides | 90 | 92 |
|  | Free Fatty Acids | 3 | 1 |
|  | Phospholipid | 1 | 0 |
| Residue after Extraction | Triglycerides | 0 | 1 |
|  | Free Fatty Acids | 0 | 1 |
|  | Phospholipid | 99 | 97 |

As a result, it was confirmed that triglycerides were predominately extracted in the extracting method regardless of the dried state of the thermally coagulated product (the solids containing lipids) and that, in the residue after the extraction, phospholipid was predominately concentrated.

EXAMPLE 9

Fish Body Size of Antarctic Krill and Heating Treatment of Squeezed Liquid

Antarctic krill with a length of 30 mm to 44 mm (20 kg) which was fished in the Antarctic Ocean during April to August of 2007 followed by an immediate freezing at −30° C. was thawed with airing for one night in a freezer (4° C.). The thawed krill were squeezed at the squeezing rate (yield of the squeezed liquid to the supplied amount of the thawed krill) of 40 to 45% by weight using a filter screw press (manufactured by Arai Machinery; type MM-2). About 5 kg of the resulting squeezed liquid was heated in a 50-L steaming type heating kettle of (rice boiler) and, when the temperature was confirmed to reach 95° C., the heating was stopped. The resulting thermally coagulated product (the solids containing lipids) was classified by a natural dropping method using a commercially available sieve basket made of stainless steel. The same experiment was performed times using different lots of krill components of the raw material and of the resulting thermally coagulated product are shown in Table 14 and Table 15, respectively. Additionally, lipid composition and fatty acid composition of the thermally coagulated product are shown in Table 16.

TABLE 14

|  |  | Lot 7 | Lot 8 | Lot 9 |
|---|---|---|---|---|
| Water | (wt %) | 81.8 | 83.5 | 82.1 |
| Total Lipids | (dry wt %) | 15.9 | 12.1 | 15.6 |
| Crude Proteins | (dry wt %) | 67.0 | 69.7 | 67.6 |
| Ash | (dry wt %) | 15.9 | 17.6 | 16.2 |
| Crude Fiber | (dry wt %) | 2.2 | 2.4 | 2.8 |

TABLE 15

|  |  | Lot 7 | Lot 8 | Lot 9 |
|---|---|---|---|---|
| Water | (wt %) | 78.9 | 79.2 | 76.5 |
| Total Lipids | (dry wt %) | 37.9 | 30.8 | 33.2 |
| Crude Proteins | (dry wt %) | 59.2 | 65.9 | 63.8 |
| Ash | (dry wt %) | 10.9 | 12.5 | 11.1 |

TABLE 16

| Material Lot |  | Lot 7 | Lot 8 | Lot 9 |
|---|---|---|---|---|
| Lipid Composition | Triglycerides | 39.9 | 29.4 | 33.5 |
|  | Free Fatty Acids | 8.7 | 8.5 | 8.4 |
|  | Phospholipid | 49.0 | 59.7 | 54.7 |
| Fatty Acid Composition | C14:0 | 10.4 | 9.5 | 10.8 |
|  | C16:0 | 19.0 | 20.9 | 21.5 |
|  | C18:1 | 15.6 | 18.7 | 19.2 |
|  | C18:2 | 2.1 | 1.8 | 1.8 |
|  | C18:3 | 1.8 | 1.2 | 1.0 |
|  | C18:4 | 4.4 | 2.1 | 1.9 |
|  | EPA | 15.2 | 15.0 | 14.1 |
|  | DHA | 8.4 | 8.8 | 7.6 |

EXAMPLE 10

Mass Production of Thermally Coagulated Product of Squeezed Krill Liquid (1)

10 tons of Antarctic krill at least 45 mm in length caught in the Antarctic Ocean in late March 2008 was squeezed using a meat separator (manufactured by Baader; type: BAADER 605) immediately after being caught to give 3 tons of squeezed liquid. This squeezed liquid was treated in an instantaneous heating and drying device (CD-500 CD dryer manufactured by Nishimura Works Co., Ltd.) to give 1080 kg of thermally coagulated product. Components in the resulting thermally coagulated products are shown in Tables 17 and 18. Dry weight (%) means the weight percentage of each component relative to the weight obtained by subtracting the weight of water from the overall weight (unless indicated otherwise, this is also the case in the subsequent examples). In addition, similar experiments were carried out five times using similar methods with a total of five lots produced between March and April of the same year, and the average values and standard deviations of these lots are shown in Tables 17 and 18.

With regard to the lipid composition, each lipid component separated by a developing solvent of benzene:chloroform:acetic acid (150:60:1.5) was quantified using a thin-layer automatic detecting device (manufactured by Mitsubishi Kagaku Iatron; type Iatroscan (registered trade mark) MK-6). With regard to the fatty acid composition, the constituting fatty acids were made into methyl esters in boron trifluoride and analyzed by a gas chromatography (Agilent Technologies; type 6890 N). The column for the gas chromatography used therefor was DB-WAX (Catalog No. 122-7032) of J &

W Scientific. With regard to a carrier gas, helium was used and hydrogen flame ionization detector was used as a detector.

TABLE 17

|  |  | Late March | March to April average ± SD* |
|---|---|---|---|
| Water | (%) | 62.4 | 66.6 ± 3.3 |
| Total Lipids | (dry wt %) | 49.6 | 45.5 ± 7.3 |
| Crude Proteins | (dry wt %) | 38.8 | 42.0 ± 4.3 |
| Ash | (dry wt %) | 11.8 | 11.6 ± 1.7 |

*SD = Standard Deviations

TABLE 18

|  |  | Late March | March to April average ± SD |
|---|---|---|---|
| Lipid Composition (%) | TG | 39.3 | 36.3 ± 2.5 |
|  | FFA | 1.8 | 2.2 ± 0.4 |
|  | PL | 57.2 | 57.2 ± 0.3 |
| Fatty Acid Composition (%) | C14:0 | 10.3 | 10.6 ± 0.2 |
|  | C16:0 | 19.3 | 19.4 ± 0.2 |
|  | C18:1 | 7.4 | 13.7 ± 4.5 |
|  | C18:2 | 2.0 | 2.1 ± 0.0 |
|  | C18:3 | 1.9 | 1.8 ± 0.1 |
|  | C18:4 | 4.7 | 4.7 ± 0.2 |
|  | EPA | 17.2 | 16.3 ± 0.7 |
|  | DHA | 9.0 | 8.5 ± 0.4 |

EXAMPLE 11

Mass Production of Thermally Coagulated Product of Squeezed Krill Liquid (2)

10 tons of Antarctic krill at least 45 mm in length collected in the Antarctic Ocean in mid-June of 2008 were squeezed using a meat separator (manufactured by Baader; type: BAADER 605) immediately after being caught to give 3 tons of squeezed liquid. 800 kg of this squeezed liquid was placed in a stainless steel tank and heated by directly introducing steam at 140° C. After heating for approximately 60 minutes, it was confirmed that the temperature had reached 85° C., and the heating was then stopped. A valve in the bottom of the tank was opened, the liquid component was removed by being allowed to pass through a mesh having an aperture size of 2 mm by means of gravity, the solid component (thermally coagulated product) was washed by being showered with an equal quantity of water, and 12 kg batches of the thermally coagulated product were placed in aluminum trays and rapidly frozen using a contact freezer. Components in the resulting thermally coagulated products are shown in Tables 19 and 20. In addition, similar experiments were carried out eight times using a total of eight lots produced between May and August 2008, and the average values and standard deviations of these lots are shown in Tables 19 and 20. Moreover, in these tables, TG denotes triglycerides, FFA denotes free fatty acids, and PL denotes phospholipids.

TABLE 19

|  |  | Late June | May to August average ± SD* |
|---|---|---|---|
| Water | (%) | 76.9 | 77.8 ± 2.0 |
| Total Lipids | (dry wt %) | 47.6 | 43.7 ± 6.7 |
| Crude Proteins | (dry wt %) | 40.3 | 39.8 ± 5.7 |
| Ash | (dry wt %) | 11.3 | 12.4 ± 1.3 |

*SD = Standard Deviations

TABLE 20

|  |  | Late June | May to August average ± SD* |
|---|---|---|---|
| Lipid Composition (%) | TG | 41.3 | 41.4 ± 1.7 |
|  | FFA | 1.7 | 1.7 ± 0.4 |
|  | PL | 52.7 | 54.1 ± 1.3 |
| Fatty Acid Composition (%) | C14:0 | 11.8 | 11.4 ± 0.5 |
|  | C16:0 | 21.7 | 21.0 ± 0.8 |
|  | C18:1 | 18.8 | 18.2 ± 1.0 |
|  | C18:2 | 1.4 | 1.5 ± 0.2 |
|  | C18:3 | 1.1 | 1.2 ± 0.2 |
|  | C18:4 | 2.3 | 2.6 ± 0.7 |
|  | EPA | 13.8 | 14.2 ± 0.7 |
|  | DHA | 6.2 | 6.7 ± 0.8 |

EXAMPLE 12

Washing and Drying of Thermally Coagulated Product 300 kg of the thermally coagulated product produced in example 11 and then stored in a freezer for 3 months was ground using a frozen cutter (FZ manufactured by Shonan Sangyo Co., Ltd.) and then placed in a nylon bag (20 mesh). This mesh bag was immersed in 900 liters of warm water at 75° C. and allowed to remain in the water for 60 minutes (final temperature: 36° C.). Next, the ground thermally coagulated product was treated in a centrifugal dehydrator (O-30 centrifugal separator manufactured by Tanabe, 60 seconds), and the bag was then immersed in 900 liters of (freshly prepared) warm water at 75° C. and allowed to remain in the water for 40 minutes (final temperature: 61° C.). The final salt concentration in the immersed liquid was then measured using a refractometer (manufactured by ATAGO) and recorded as 0.12%. The bag was again treated using a centrifugal dehydrator (1 minute) and solids (water content: 67%) were removed from the bag. 300 g of tocopherol was added to these solids, blended in a mixer and then dried under stirring over a period of 4 hours by means of a hot air flow at 60° C. As a result, 48.08 kg of washed and dried product having a water content of 2.9% and a final product temperature of 54° C. was obtained. Components in the resulting washed and dried product are shown in Tables 21 and 22. In addition, similar experiments were carried out 27 times, and the average values and standard deviations of 27 lots of washed and dried products produced using the same process are shown in Tables 21 and 22.

TABLE 21

|  |  | Thermally Coagulated Product | Washed and Dried Product | Washed and Dried Products (27 lots) |
|---|---|---|---|---|
| Water | (%) | 75.6 | 3.6 | 2.1 ± 1.2 |
| Total Lipids | (dry wt %) | 43.4 | 50.9 | 49.9 ± 2.5 |
| Crude Proteins | (dry wt %) | 41.0 | 46.4 | 45.3 ± 2.0 |
| Ash | (dry wt %) | 15.6 | 4.4 | 4.3 ± 0.3 |

TABLE 22

|  |  | Thermally Coagulated Product | Washed and Dried Product | Washed and dried Products (27 lots) |
|---|---|---|---|---|
| Fatty Acid Composition (%) | C14:0 | 11.7 | 11.8 | 11.1 ± 0.5 |
|  | C16:0 | 20.8 | 21.2 | 20.3 ± 0.8 |
|  | C18:1 | 18.3 | 18.6 | 17.7 ± 1.0 |
|  | C18:2 | 1.4 | 1.4 | 1.5 ± 0.2 |
|  | C18:3 | 1.1 | 1.1 | 1.3 ± 0.3 |
|  | C18:4 | 2.2 | 2.3 | 2.6 ± 0.7 |
|  | EPA | 13.7 | 13.9 | 14.1 ± 0.7 |
|  | DHA | 6.1 | 6.3 | 6.8 ± 0.7 |

EXAMPLE 13

Washing and Drying of Thermally Coagulated Product 1 ton of thermally coagulated product produced in example 11 and then stored for 3 months in a freezer was placed in 3000 liters of water, heated under stirring, and then held for 10 minutes at a temperature of 65° C. The water was removed via 24 mesh nylon, and the solid component was placed in 3000 liters of water (at 20° C.). After stirring for 15 minutes, the water was removed via 24 mesh nylon, and 564 kg of solid component (water content 73%) was obtained by treating for 15 seconds in a centrifugal dehydrating machine (manufactured by Tanabe; type O-30). 1.54 kg of tocopherol was added to this solid component, blended in a mixer, and then dried for 3.2 hours at a hot air temperature of 60° C. so as to obtain 148.4 kg of washed and dried product. Components in the resulting washed and dried product are shown in Tables 23 and 24.

TABLE 23

|  |  | Washed and Dried Product |
|---|---|---|
| Water | (%) | 2.1 |
| Total Lipids | (dry wt %) | 49.6 |
| Crude Proteins | (dry wt %) | 46.4 |
| Ash | (dry wt %) | 4.3 |

TABLE 24

|  |  | Washed and Dried Product |
|---|---|---|
| Fatty Acid Composition (%) | C14:0 | 10.7 |
|  | C16:0 | 20.1 |
|  | C18:1 | 17.9 |
|  | C18:2 | 1.9 |
|  | C18:3 | 1.2 |
|  | C18:4 | 2.5 |
|  | EPA | 14.0 |
|  | DHA | 6.8 |

EXAMPLE 14

Extraction of Lipids from Washed (Undried) Thermally Coagulated Product 1 ton of the thermally coagulated product produced in example 10 and then stored in a freezer for 3 months was ground using a frozen cutter and then placed in 3000 liters of hot water at 80 to 90° C. This liquid was stirred for 30 minutes while maintaining the temperature at 80 to 90° C. and then filtered with a 60 mesh filter to give solids (a). 3000 liters of hot water at 80 to 90° C. was added to the solids (a), this liquid was stirred for 30 minutes while maintaining the temperature at 80 to 90° C. and then filtered with a 60 mesh filter to give solids (b). This procedure was repeated to give solids (c) and then repeated again to give solids (d). 3000 liters of 92% ethanol was added to the solids (d), stirred for 15 minutes and dewatered using a 60 mesh filter to give solids (e) and an ethanol substitution fluid (F). 3000 liters of 92% ethanol was added to the solids (e) and refluxed for 2 hours at atmospheric pressure in order to extract the lipids. This lipid extraction liquid (G) was filtered with a 60 mesh filter to give a residue (H). 3000 liters of 92% ethanol was added to this residue (H), refluxed for 2 hours at atmospheric pressure and then treated with a 60 mesh filter to give a lipid extraction liquid (I) and a residue (J). The ethanol substitution fluid (F), lipid extraction liquid (G) and lipid extraction liquid (I) were combined, and the ethanol and water were removed by means of a vacuum concentrator to give 88 kg of extracted lipids. Components in the resulting extracted lipids are shown in Tables 25 and 25. Moreover, in Table 25, the water content was measured in accordance with section 984.20 of the AOAC International Standards (18th edition), and the phospholipids content was measured by subjecting 300 mg of a hexane solution of extracted lipids to silica gel chromatography, recovering and dissolving the adsorbed fraction with chloroform, removing the solvent under reduced pressure and then measuring the weight. In addition, parts of solids (a) and (b) were batched off, and the procedure subsequent to the addition of 92% ethanol was carried out to give comparative extraction liquids (K) and (L).

TABLE 25

|  |  | Extracted Lipids |
|---|---|---|
| Water | (%) | 0.25 |
| Ethanol | (%) | 0.57 |
| Sodium | (%) | 0.29 |
| Phospholipid | (%) | 55.2 |
| Acid Number |  | 8.19 |
| Peroxide Value | (meq/kg) | <0.1 |
| Astaxanthin | (ppm) | 128 |
| Arsenic | (ppmAs) | 5.6 |
| Lead | (ppm) | <0.05 |
| Cadmium | (ppm) | <0.01 |
| Mercury | (ppm) | <0.01 |
| Tin | (ppm) | <1 |
| PCB compounds | (ppm) | <0.1 |

TABLE 26

|  |  | Extracted Lipids |
|---|---|---|
| Fatty Acid Composition (%) | C14:0 | 9.3 |
|  | C16:0 | 19.5 |
|  | C18:1 | 14.8 |
|  | C18:2 | 2.0 |
|  | C18:3 | 2.0 |
|  | C18:4 | 4.7 |
|  | EPA | 19.6 |
|  | DHA | 10.6 |

EXAMPLE 15

Extraction of Lipids from Washed and Dried Thermally Coagulated Product 1200 liters of 99% ethanol was added to 299.6 kg of the washed and dried product produced in example 13, heated to 60° C., and stirred for 2 hours. Solid-liquid separation was then carried out by means of gravity, using 100 mesh nylon, so as to obtain an extraction liquid (A) and an extraction meal (a). 800 liters of 99% ethanol was added to the extraction meal (a), heated to 60° C. and stirred for 2 hours, after which solid-liquid separation was then carried out using 100 mesh nylon so as to obtain an extraction liquid (B) and an extraction meal (b). 700 liters of 99% ethanol was added to the extraction meal (b), heated to 60° C., and stirred for 2 hours, after which solid-liquid separation was then carried out using 100 mesh nylon so as to obtain an extraction liquid (C) and 390 kg of an extraction meal (c) (the reduction in weight after drying at 105° C. for 4 hours was 61.8%). When the extraction liquid (A), extraction liquid (B), and extraction liquid (C) were combined, the total weight thereof was 2089 kg. These combined extraction liquids were concentrated under reduced pressure at a temperature of 60° C. or lower, and the ethanol and water were removed so as to obtain 141.6 kg of extracted lipids. Components in the resulting extracted lipids are shown in Tables 27 and 28.

TABLE 27

|  |  | Extracted Lipids |
|---|---|---|
| Water | (%) | 0.41 |
| Ethanol | (%) | 0.21 |
| Sodium | (%) | 0.10 |
| Phospholipid | (%) | 44.8 |
| Acid Number |  | 4.22 |
| Peroxide Value | (meq/kg) | <0.1 |
| Astaxanthin | (ppm) | 377 |

TABLE 28

|  |  | Extracted Lipids |
|---|---|---|
| Fatty Acid Composition (%) | C14:0 | 8.2 |
|  | C16:0 | 19.4 |
|  | C18:1 | 15.1 |
|  | C18:2 | 1.9 |
|  | C18:3 | 1.4 |
|  | C18:4 | 2.3 |
|  | EPA | 18.8 |
|  | DHA | 11.7 |

EXAMPLE 16

Extraction of Lipids from Washed and Dried Thermally Coagulated Product 210 liters of 95% ethanol was added to 70 kg of the washed and dried thermally coagulated product produced in example 12 and stirred for 2 hours at 50° C. Solid-liquid separation was then carried out by means of gravity, using 60 mesh nylon, to give an extraction liquid (A) and a solid (a). 210 liters of 95% ethanol was added to the solid (a) and stirred for 2 hours at 50° C. Solid-liquid separation was then carried out by means of gravity, using 60 mesh nylon, to give an extraction liquid (B) and a solid (b). 210 liters of 95% ethanol was added to the solid (b) and stirred for 2 hours at 50° C. Solid-liquid separation was then carried out by means of gravity, using 60 mesh nylon, to give an extraction liquid (C) and a solid (c) (residue following extraction: 58.7 kg). The extraction liquid (A), extraction liquid (B), and extraction liquid (C) were combined and concentrated under reduced pressure after removing fine solids therefrom by means of a filter paper to give 24.0 kg of extracted lipids. Components in these extracted lipids are shown in Tables 29 and 30.

TABLE 29

|  |  | Extracted Lipids |
|---|---|---|
| Water | (%) | 0.49 |
| Ethanol | (%) | 0.02 |
| Sodium | (%) | 0.11 |
| Phospholipid | (%) | 55.2 |
| Acid Number |  | 4.82 |
| Peroxide Value | (meq/kg) | <0.1 |
| Astaxanthin | (ppm) | 172 |
| Arsenic | (ppmAs) | 6.2 |
| Lead | (ppm) | <0.05 |
| Cadmium | (ppm) | <0.01 |
| Mercury | (ppm) | <0.01 |
| Tin | (ppm) | <1 |
| PCB compounds | (ppm) | <0.1 |

TABLE 30

|  |  | Extracted Lipids |
|---|---|---|
| Fatty Acid Composition (%) | C14:0 | 10.4 |
|  | C16:0 | 20.8 |
|  | C18:1 | 16.3 |
|  | C18:2 | 1.5 |
|  | C18:3 | 1.7 |
|  | C18:4 | 2.4 |
|  | EPA | 16.4 |
|  | DHA | 7.7 |

EXAMPLE 17

Comparison of Lipid Weights in Thermally Coagulated Products of Squeezed Krill Liquids (Live) krill collected in the Antarctic Ocean between June and July 2008 and then frozen were allowed to thaw to room temperature. This krill was squeezed using 30 mesh nylon at a squeezing ratio required to obtain squeezed liquids corresponding to an amount of 5 to 53% of the total weight. Each obtained squeezed liquid was heated at 85° C. or higher for 5 minutes so as to produce thermally coagulated products. In addition, the thermally coagulated product obtained from a squeezed liquid having a squeezing ratio of 50% was washed twice with a quantity of water corresponding to twice the quantity of the thermally coagulated product, and the resulting washed product was dried for 4 hours while being agitated with hot air at 60° C. so as to obtain a washed and dried product of the thermally coagulated product. The analysis values for each thermally coagulated product are shown in Table 31. The lipids, proteins, and ash content in the table are expressed in terms of wt. % relative to the total weight, and the water content of the thermally coagulated product was calculated by subtracting these contents from 100%. The composition of each lipid is expressed in terms of wt. % of each component relative to the overall lipid content. The total lipid content is expressed in terms of wt. % of the lipid relative to the total solid content, that is, to the total weight of lipids, proteins, and ash.

TABLE 31

|  |  | A | B | C | D | E |
|---|---|---|---|---|---|---|
| Water | (%) | 77.8 | 77.5 | 81.3 | 81.7 | 2.4 |
| Lipids | (%) | 8.7 | 7.8 | 6.7 | 6.3 | 46.0 |
| Crude Proteins | (%) | 11.3 | 12.4 | 9.8 | 9.8 | 44.9 |
| Ash | (%) | 2.2 | 2.3 | 2.2 | 2.2 | 4.2 |
| Fatty Acid | C14:0 | 10.8 | 1.0 | 11.2 | 11.0 | 11.1 |

TABLE 31-continued

|  |  | A | B | C | D | E |
|---|---|---|---|---|---|---|
| Composition | C16:0 | 20.0 | 20.4 | 20.1 | 19.9 | 20.2 |
|  | C18:1 | 18.7 | 18.9 | 18.6 | 18.6 | 18.3 |
|  | C18:2 | 1.4 | 1.4 | 1.4 | 1.4 | 1.9 |
|  | C18:3 | 1.1 | 1.1 | 1.1 | 1.1 | 1.3 |
|  | C18:4 | 2.1 | 2.1 | 2.3 | 2.3 | 2.6 |
|  | EPA | 13.9 | 14.2 | 13.8 | 13.7 | 13.7 |
|  | DHA | 6.6 | 6.8 | 6.2 | 6.2 | 6.7 |
| Total Lipids | (%) | 39.2% | 34.7% | 35.8% | 34.4% | 48.4% |

*A: Squeezing ratio 50% coagulated product
*B: Squeezing ratio 30% coagulated product
*C: Squeezing ratio 12% coagulated product
*D: Squeezing ratio 5% coagulated product
*E: Squeezing ratio 50% washed and dried product of the coagulated product In the "Okean" (dried paste) disclosed in non-patent document 5, it is understood that the lipid content is 23.0 to 28.4%, while the total lipid content in the squeezed thermally coagulated product (dried product) is 34.4 to 48.4%, from which it is understood that the lipid content in the squeezed thermally coagulated product is extremely high.

In addition, because water-soluble proteins and ash are washed away by washing with water, it is understood that the weight percentage of lipids per solid content is higher after washing with water than before.

EXAMPLE 18

Analysis of Krill Odor and Unpleasant Odor Sources

Krill oil was extracted from the (dried) thermally coagulated product (F) shown in example 10 using a quantity of 99.8% ethanol equivalent to 9 times the quantity of the thermally coagulated product (F).

A quantity of distilled water equivalent to 15 times the quantity of this extraction liquid was added thereto and heated, the resulting steam was trapped and adsorbed on a Porapak Q (manufactured by Waters, 50 to 80 mesh), and eluted with diethyl ether to give a krill odor sample.

Using GC set to the conditions shown in Table 32, the krill odor component fractions in this krill odor sample were confirmed by sniffing.

TABLE 32

| GC apparatus | GC14A (Shimadzu Corporation) |
|---|---|
| GC column | DB-WAX (0.53 mm i.d. × 30 m, film thickness 1.00 μm) |
| Preparative capillary fragments | DB-WAX (0.32 mm i.d. × 10 m, film thickness 1.00 μm) |
| Column temperature | 50° C → 230° C (held for 20 minutes) (5° C./min) |
| Injection port temperature | 230° C. |
| Injection quantity | 2 μL |
| Carrier gas | He |
| Detector temperature | 250° C. |
| Detection method | Hydrogen flame ionization detector |

As a result, chromatograms such as that shown in FIG. 1 were obtained, and when the krill odor was sniffed, a characteristic krill odor was sensed in fractions (Fr) 3 and 4, as shown in Table 33.

TABLE 33

| Fr. | Odor Characteristics | Intensity |
|---|---|---|
| 1 | Almost no odor | Faint |
| 2 | Metallic | Faint |

TABLE 33-continued

| Fr. | Odor Characteristics | Intensity |
|---|---|---|
| 3 | Unpleasant, aldehyde-like | Intense |
| 4 | Stays inside the nose, burning odor, unpleasant | Intense |
| 5 | Slight burning odor, unpleasant, aldehyde-like | Medium |
| 6 | Almost no odor | Faint |

EXAMPLE 19

Sensory Test for Extracted Lipids

The krill oil extracted in example 18 was used as sample 1, the krill odor sample obtained in example 18 was used as sample 2, the lipids extracted in example 14 were used as sample 3, the lipids extracted in example 15 were used as sample 4, and the lipids extracted in example 16 were used as sample 5. 50 ml of each sample was placed in a vial and evaluated in terms of odor by six subjects. The result is shown in Table 34.

TABLE 34

|  | Stays inside the nose, burning odor, unpleasant | Slight burning odor, unpleasant, aldehyde-like |
|---|---|---|
| 1 | Intense | Intense |
| 2 | Intense | Intense |
| 3 | Faint | Faint |
| 4 | Medium | Medium |
| 5 | Faint | Faint |
| 6 | Faint | Medium |
| 7 | Faint | Medium |

From these results, it is thought that in cases where extraction liquids are extracted using super-heated steam, krill odors and unpleasant odors that occur when lipids are extracted from krill are components that are trapped in a Porapak Q column and that krill odor and unpleasant odor sources can be eliminated by washing with water prior to extracting lipids from thermally coagulated products.

Industrial Applicability

The present invention is useful as a method for producing of lipids which abundantly contain phospholipid easily and at a low cost. In addition, lipids extracted using this method and compositions containing large quantities of useful lipids derived from crustaceans are useful as medical raw materials, food materials, raw materials for feedstuffs and the like.

The invention claimed is:

1. A solid composition containing lipids obtained by the following steps in the following order squeezing a whole crustacean so as to break down tissue of the whole crustacean and to obtain a squeezing liquid,
    heating the squeezed liquid to a temperature at which the proteins contained in the squeezed liquid coagulate, wherein the temperature is 50° C. or more,
    carrying out solid-liquid separation so as to separate the heated squeezed liquid into a solid component that contains lipid components and an aqueous component that contains water-soluble components, and
    washing the resulting solid containing lipids or a dried product thereof with water, followed by dehydrating and/or drying,
    wherein the solid-liquid separation is carried out by at least one selected from the group consisting of filtration and centrifugal separation.

2. The composition containing lipids of claim 1, from which components adsorbed using a column that adsorbs volatile components having molecular weights of 100 to 200 are removed to an extent whereby odors from these components cannot be sensed in a sensory test, wherein the sensory test includes a determination as to whether a subject senses an odor from 50 ml of lipids.

3. The composition containing lipids of claim 1, wherein the whole crustacean or the part thereof is squeezed using at least one selected from the group consisting of an oil hydraulic squeezing machine, a screw press, a meat separator, a press dehydrating machine and a centrifugal separator.

4. The composition containing lipids of claim 1, wherein the squeezed liquid is heated at a temperature of less than or equal to 150° C.

\* \* \* \* \*